(12) United States Patent
Wang et al.

(10) Patent No.: US 7,245,371 B2
(45) Date of Patent: Jul. 17, 2007

(54) LASER CURING APPARATUS WITH REAL-TIME MONITORING AND CONTROL

(75) Inventors: Sean Xiaolu Wang, Centerville, DE (US); Qun Li, Newark, DE (US); Qingxiong Li, Newark, DE (US)

(73) Assignee: B & W Tek, Inc., Newark, DE (US)

(*) Notice: Subject to any disclaimer, the term of this patent is extended or adjusted under 35 U.S.C. 154(b) by 12 days.

(21) Appl. No.: 11/212,124

(22) Filed: Aug. 26, 2005

(65) Prior Publication Data

US 2006/0044555 A1 Mar. 2, 2006

Related U.S. Application Data

(60) Provisional application No. 60/604,711, filed on Aug. 27, 2004.

(51) Int. Cl.
*G01N 21/65* (2006.01)
*G01N 21/64* (2006.01)

(52) U.S. Cl. ...................... 356/301; 356/318

(58) Field of Classification Search .............. 356/301
See application file for complete search history.

(56) References Cited

U.S. PATENT DOCUMENTS

| | | | |
|---|---|---|---|
| 4,399,100 A | 8/1983 | Zsolnay et al. | |
| 4,874,948 A | 10/1989 | Cielo et al. | |
| 4,891,591 A | 1/1990 | Johnston et al. | |
| 4,921,415 A | 5/1990 | Thomas, III et al. | |
| 5,100,802 A | 3/1992 | Mickols | |
| 5,606,171 A | 2/1997 | Neckers et al. | |
| 5,911,159 A | 6/1999 | Choo et al. | |
| 5,955,002 A | 9/1999 | Neckers et al. | |
| 6,456,895 B1 | 9/2002 | Aloisio, Jr. et al. | |

FOREIGN PATENT DOCUMENTS

| | | |
|---|---|---|
| EP | 1 353 168 | 10/2003 |
| WO | WO 97/19325 | 5/1997 |
| WO | WO 00/34770 | 6/2000 |
| WO | WO 02/06620 | 1/2002 |

OTHER PUBLICATIONS

Lyon et al, In Situ Cure Monitoring of Epoxy Resins Using Fiber-Optic Raman Spectroscopy, Journal of Applied Polymer Science, vol. 53, 1805-1812 (1994).*

Soares et al, Vicker's hardness and Raman spectroscopy evaluation of a dental composite cured by an argon laser and a halogen lamp, Journal of Biomedical Optics, vol. 9, No. 3, 601-608 (May/Jun. 2004).*

* cited by examiner

*Primary Examiner*—F. L. Evans
(74) *Attorney, Agent, or Firm*—Blank Rome LLP

(57) ABSTRACT

In a laser based curing apparatus, the acts both as the curing light and the excitation source for a Raman spectroscopic sensor. The spectroscopic sensor provides real-time, in situ, non-invasive curing status monitoring via Raman spectroscopy. The spectroscopic information can be further used to control the operation parameters of the laser to achieve the optimum cure result.

26 Claims, 3 Drawing Sheets

LASER CURING APPARATUS WITH REAL-TIME MONITORING AND CONTROL

REFERENCE TO RELATED APPLICATION

The present application claims the benefit of U.S. Provisional Application No. 60/604,711, filed Aug. 27, 2004, whose disclosure is hereby incorporated by reference in its entirety into the present disclosure.

FIELD OF THE INVENTION

This invention generally relates to a curing apparatus, and more specifically to a laser based curing apparatus with real-time monitoring and control by means of Raman spectroscopy.

DESCRIPTION OF RELATED ART

The rapid development of solid state lasers makes it possible to replace the conventional lamp based curing light source with a compact, highly efficient, low power-consumption laser based curing light source. The laser based curing light source is suitable for many applications including but not limited to high precision assembly, dental resin curing, and micro-biomedical devices. Such applications require accurate and fast curing with optimum curing condition, such as low shrinkage, high strength, low outgassing, and minimum lateral heat generation. For these applications, it is highly desirable to monitor the curing status of the material in real time as to achieve the optimum performance and maximum productivity.

The prior art for cure monitoring can be divided into three categories. The first category relates to those off-line examination methods such as hardness and shear strength test. The second category relates to those methods utilizing embedded sensors. For example, PCT international patent application No. WO02066220 and U.S. Pat. No. 6,456,895 describe thermal sensors to measure temperature change of the material being cured. U.S. Pat. Nos. 5,955,002, 5,100,802 and 5,606,171 disclose methods of employing fluorescence probes for cure monitoring. PCT international patent application No. WO9719325 teaches a fiber grating sensor based cure monitoring method. U.S. Pat. Nos. 4,921,415 and 5,911,159 disclose ultrasonic probes for cure monitoring. The third category of cure monitoring methods relates to measurement of certain physical parameters of the material during cure process. For example, PCT international patent application No. WO0034770 teaches a method of using compression wave induced resonant vibration to indicate the curing progression. European patent No. 1353168 and U.S. Pat. Nos. 4,891,591 and 4,399,100 describe electromagnetic cure monitoring devices measuring the resistance or dielectric change of the material. U.S. Pat. No. 4,874,948 discloses a non-contact temperature sensor for evaluating the degree of cure.

Recently, it has been demonstrated that the Raman spectroscopic technique can be used as a tool for in situ, non-invasive cure status monitoring. In one article titled "Process cure monitoring of unsaturated polyester resins, vinyl ester resins, and gel coats by Raman spectroscopy" in *Journal of Applied Polymer Science*, Vol. 93, 2004, Mikael Skrifvars et al. measured the Raman signal that corresponds to C=C bond (1620 $cm^{-1}$) and used its ratio to the C=O bond to accurately monitor the curing process. An 830 nm laser with 300 mW output power was used as the excitation light source. In another article titled "Precise determination of percent cure of epoxide polymers and composites via fiber-optic Raman spectroscopy and multivariate analysis" in *Applied Spectroscopy*, Vol. 51, 1997, Jeffrey F. Aust et al. utilized the C—H stretching mode (2870–3000 $cm^{-1}$) to determine the degree of cure. A 30 mW 488 nm argon laser was used as the excitation light source. Similar reports were also published in the application notes of many Raman spectroscopy equipment manufacturers, such as Real-Time Analyzers.

The difficulty of using Raman spectroscopy for cure monitoring lies in its high cost. An additional high power laser with very narrow linewidth and an ultra sensitive spectrometer are generally required for the Raman spectroscopic monitor. Both of them are very expensive for a curing system.

SUMMARY OF THE INVENTION

It is an object of the invention to overcome the above-noted deficiencies of the prior art.

To achieve the above and other objects, the present invention is directed to a laser based curing apparatus with a Raman spectroscopic sensor for real-time, non-invasive cure monitoring and control. Unlike previous approaches, the curing laser itself is used as the Raman excitation light source in the current invention. Since no additional laser is required, the cost of the monitoring system is greatly reduced. The power requirement for the curing laser is generally in several mW to hundreds of mW range depending on the material and the size of the curing area. This power is strong enough to generate significant Raman emission. In addition, as the wavelength of the curing laser is generally selected to match with the absorption band of the material, the resonant Raman effect may be employed in which, the Raman emission can be enhanced by 1000–10000 times. All these greatly reduce the requirement for the sensitivity of the spectrometer, making it possible to use a low-cost spectrometer for cure status monitoring.

It is thus one goal of the current invention to provide a laser based light source for high precision curing of a material. The laser can be a semiconductor laser diode (LD), a diode pumped solid-state laser (DPSSL), or other kinds of lasers. Depending on the material to be cured, the emission wavelength of the laser can be either in ultraviolet/visible (UV/VIS) range for photochemical curing or in near infrared/infrared (NIR/IR) range for thermal curing. The laser has a narrow linewidth that can perfectly match with the absorption peak of the material, which results in a better curing efficiency than that of conventional lamps. The intrinsic beam size of the laser is small, which is ideal for applications that require accurate spot curing. The beam size of the laser can also be expanded using a secondary optical system to adapt for other applications. Depending on the requirement for different materials, the laser can work either in continuous wave (CW) mode or in pulsed mode by direct or external modulation technique. The pulse width and repetition rate of the laser can be controlled to match with the thermal relaxation cycle of the material as to achieve the best curing result in bond strength, surface hardness, material shrinkage, curing speed and heat generation.

It is another goal of the current invention to utilize a spectroscopic sensor to measure the Raman emission of the material during the cure process, which Raman emission is excited by the curing laser itself. The Raman signal, which contains structural information of the material, is further used as an indicator to monitor the curing status. The spectroscopic sensor can be a general-purpose spectrometer that composed of wavelength selective components (such as gratings, interferometers, tunable filters) and photo detectors or photo detector arrays. Or it can be a special-purpose spectrometer having several fixed filters and photo detectors to measure the Raman signal at certain characteristic wavelengths.

It is yet another goal of the current invention to utilize the obtained Raman signal to control the curing profile of the laser, which includes laser power, intensity, pulse width, duty cycle, and/or repetition rate variation with time, in order to further improve the curing result. Based on previous research results, many materials cure best under varied light exposure during the cure process. Once the spectroscopic sensor indicates that the curing reaches its optimum condition, the laser can be automatically turned off by the feedback control system to avoid over-curing.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENTS

Preferred embodiments of the present invention will now be set forth in detail with reference to the drawings.

Figure 1:
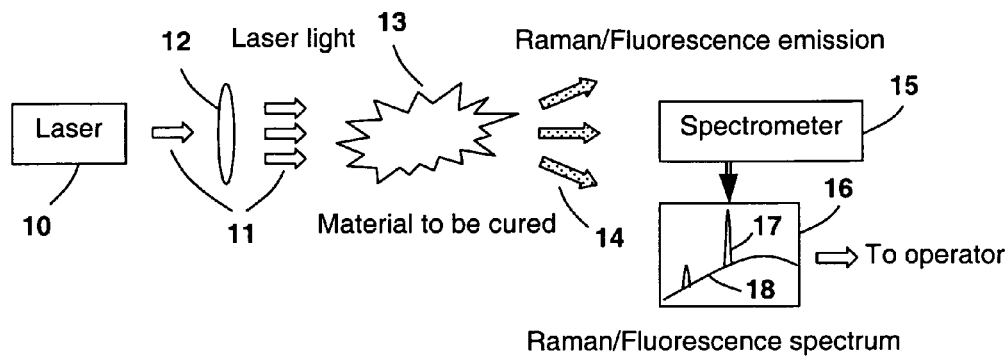
FIG. 1(a) shows a schematic representation of the laser curing apparatus with spectroscopic sensor for real-time cure monitoring.
FIG. 1(b) shows another representation of the laser curing apparatus with spectroscopic sensor for real-time cure monitoring and control.
FIG. 1(c) shows a schematic diagram of the spectrometer element of FIG. 1(a) or (b).
Figure 1:
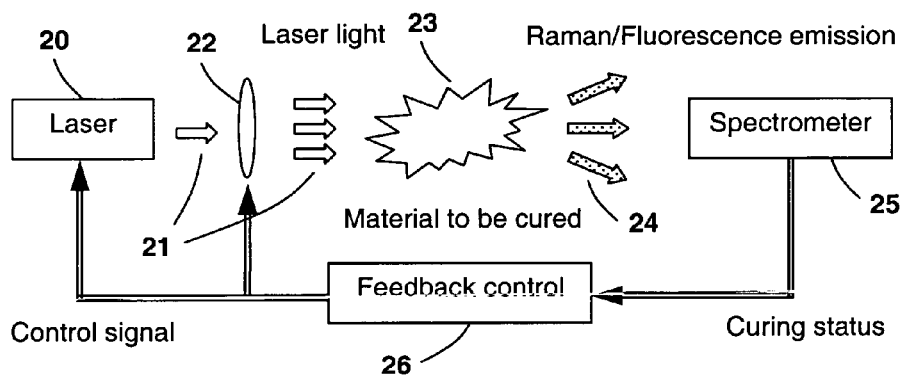
Figure 1:
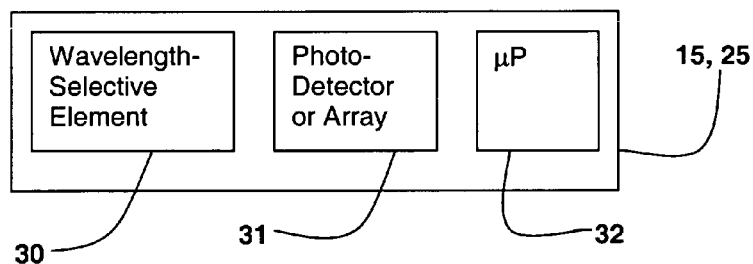

A schematic representation of the laser curing apparatus is shown in FIGS. 1(a) and (b). In FIG. 1(a), the curing laser 10 produces laser light 11, which is first transformed (focused, expanded, collimated) by a secondary optical system 12 and then absorbed by the material 13 to induce and/or accelerate the polymerization process. The laser light 11 in the mean time excites Raman/fluorescence emission 14 from the material 13 during the cure process. An optical spectrometer 15 is used to collect and analyze the Raman/fluorescence signal and produces a Raman/fluorescence spectrum 16, which is composed of Raman signal 17 and fluorescence background 18. The intensity and wavelength position of the Raman signal 17 are used to determine the curing status of the material in real time since the Raman signal 17 is directly related to the vibration/rotational energy levels of the material 13, which energy levels will vary during the cure process. The curing status is finally sent to an operator for further actions. In FIG. 1(b), the curing laser 20 produces laser light 21, which is first transformed by a secondary optical system 22 and then cures material 23 and produces Raman/fluorescence emission 24 in a similar way as shown in FIG. 1(a). The detected Raman signal by the spectrometer 25 is used control the secondary optical system 22 and the operation parameters of the laser 20, i.e., regulating the power, intensity, pulse width, duty cycle, and/or repetition rate of the laser light 21 during the cure process through a feedback control system 26 to achieve the optimum curing result.

As shown in FIG. 1(c), the spectrometer 15 or 25 includes a wavelength-selective element or elements 30, one or more photodetectors or photodetector arrays 31, and a microprocessor 32 capable of performing the calculations needed to carry out the operations disclosed herein for the present invention. For a general-purpose spectrometer, the wavelength-selective element or elements 30 can be gratings, interferometers, tunable filters, or the like. For a special-purpose spectrometer, the wavelength-selective elements 30 can be fixed filters to allow the photodetectors 31 to measure the Raman signal at certain characteristic wavelengths.

Figure 2:
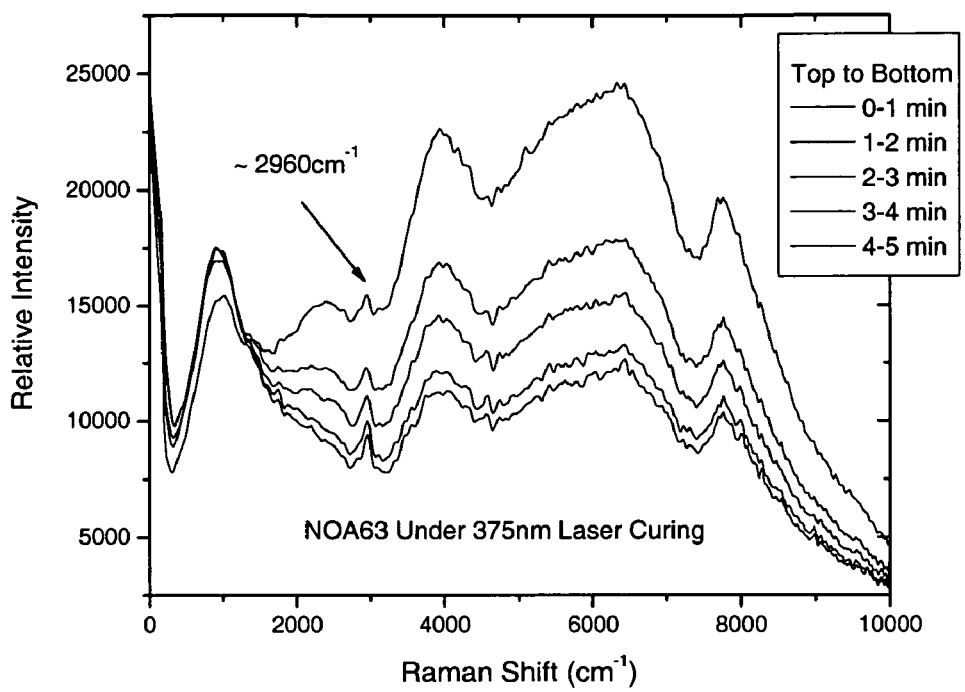
FIG. 2(a) shows the Raman/fluorescence spectra of a UV adhesive excited by a 375 nm curing laser.
FIG. 2(b) shows the intensity variation of the C—H band Raman signal for the UV adhesive during the cure process.
Figure 2:
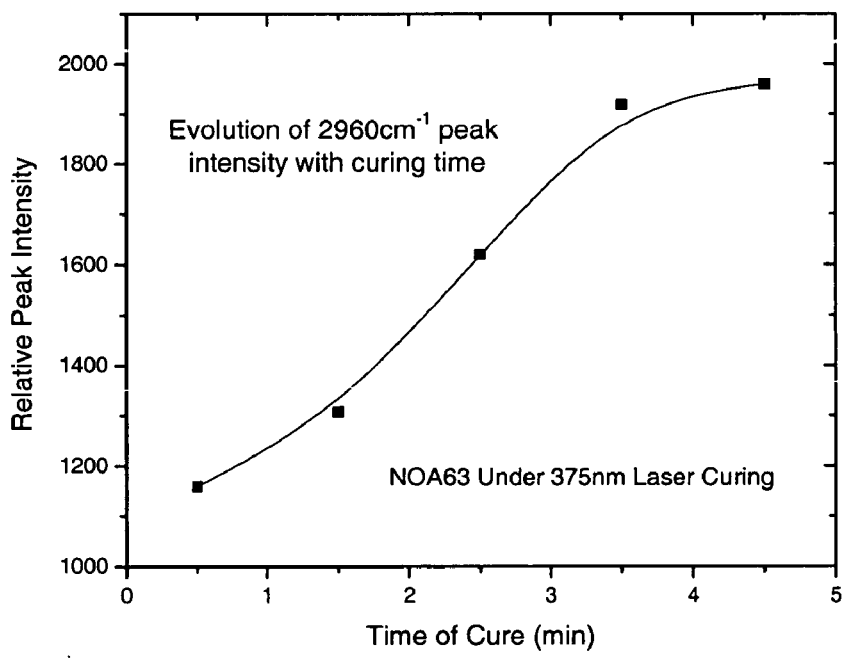

In the first exemplary embodiment of the current invention, a 375 nm UV laser diode with 5 mW output power and <1 nm linewidth is used as the curing and Raman excitation light source. The material to be cured is a UV curable optical adhesive manufactured by Norland Products Inc. with product No. of NOA63. The adhesive is in liquid form before cure and is transparent in the visible wavelength range. Full cure of the adhesive requires a curing time of 5 minutes according to its specification. In this exemplary embodiment, the laser beam is first collimated into a beam size of 1.5 mm and then directed to the adhesive sample. The laser light is absorbed by the adhesive and activates its photoinitiators, which trigger the polymerization process. The Raman/fluorescence emission of the adhesive sample during the polymerization process is measured in real time by a general-purpose CCD spectrometer that composed of a dispersive grating and a Si linear CCD array. The spectrometer has a measurable wavelength range of 300–750 nm and a wavelength resolution of <1 nm. The integration time of the spectrometer is set to 30 s, i.e., the spectrometer finishes one measurement in 30 s. The Raman/fluorescence emission spectrum of the adhesive sample is measured continuously by the spectrometer during a 5 minutes curing period. The obtained Raman/fluorescence spectra are shown in FIG. 2(a). The emission spectra of the adhesive show a strong broadband fluorescence background and a relatively weak narrowband Raman signal at around 2960 $cm^{-1}$, which may be caused by —$CH_3$, —$CH_2$, —CH stretching modes or their combinations as described by Jeffrey F. Aust et al. in their article. During the polymerization process, the intensity of the fluorescence background drops while the relative intensity of the Raman signal increases. The relative peak intensity of the Raman signal is determined from the Raman/fluorescence spectra and shown in FIG. 2(b). From FIG. 2(b), it can be seen that the intensity variation of the Raman signal is a good indicator of the polymerization process, which is further verified by post-cure hardness measurement.

Figure 3:
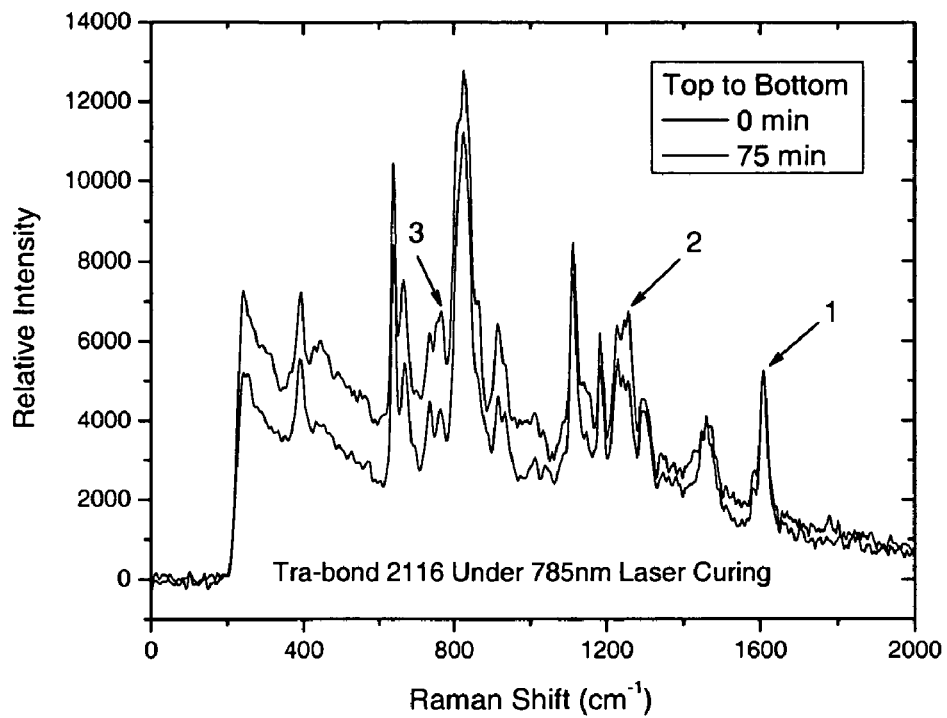
FIG. 3(a) shows the Raman/fluorescence spectra of an epoxy sample excited by a 785 nm curing laser.
FIG. 3(b) shows the intensity variation of the epoxy band Raman signal for the epoxy sample during the cure process.
Figure 3:
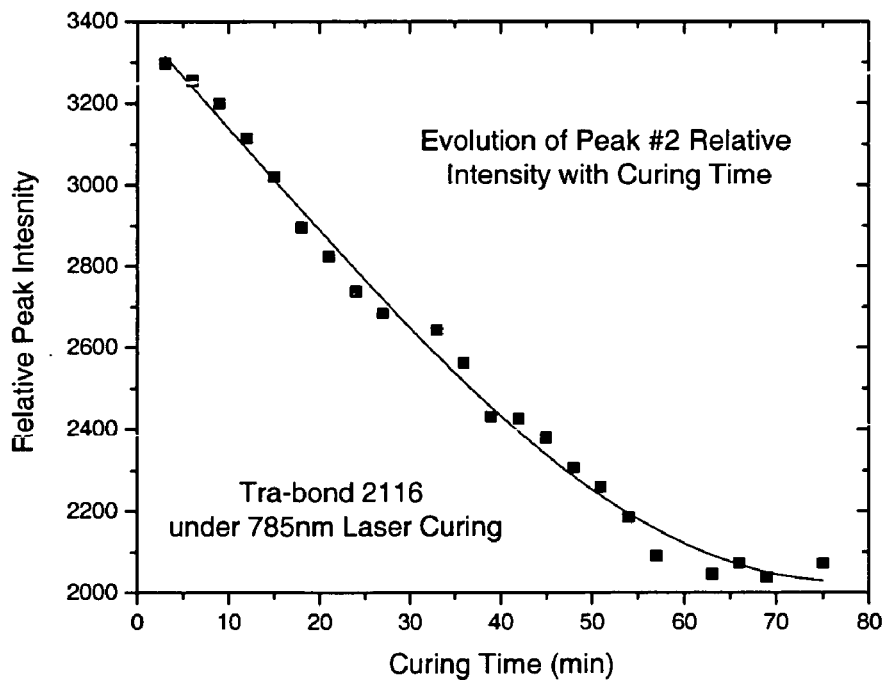

In the second exemplary embodiment of the current invention, a 785 nm NIR laser diode is used to thermally cure an epoxy sample from Tra-Con, Inc. with product No. of Tra-bond 2116. The epoxy is a gelatin-like milky-colored two-component adhesive that cures after 24 hours at 25° C. or 4 hours at 65° C. subsequent to mixing. The laser diode has an output power of 600 mW and a linewidth of <0.5 nm. A CCD spectrometer with 750–1050 nm spectral range and 10 $cm^{-1}$ spectral resolution is used to record the Raman/fluorescence emission spectrum of the epoxy during the cure process. The integration time of the spectrometer is set to 60 s. In this exemplary embodiment, the epoxy sample has a size of 3×3 mm. The laser beam is focused onto the sample surface and diffused by the epoxy material for uniform curing. The epoxy sample is heated up to a temperature of about 80° C. by the laser illumination. The Raman/fluorescence emission spectrum of the epoxy sample is recorded every 3 minutes during the 75 minutes polymerization process. The initial and final Raman/fluorescence spectra of the sample are shown in FIG. 3(a). It can be seen that the epoxy band at 1260 cm$^{-1}$ (peak #2 in FIG. 3(a)) decreases as the oxirane ring is opened by the curing reaction, while the phenyl ring stretch at 1610 cm$^{-1}$ (peak #1 in FIG. 3(a)) remains constant which can be used as a reference. The primary amine band (peak #3 in FIG. 3(a)) also decreases as it is involved in the reaction. The variation of the relative intensity of the epoxy band vs. curing time is plotted in FIG. 3(b). It can be seen that the intensity decrease of the 1260 cm$^{-1}$ epoxy band follows a Gaussian model. This matches well with the previous results published in the application note of Real-Time Analyzers, in which a FT-IR spectrometer is used to monitor the epoxy curing process. The amine band (peak #3) intensity is also a good indicator of the curing status.

The methods disclosed herein illustrate the principle of the present invention. All modifications to the embodiments describes herein without deviating from the essential idea of using the curing light source as Raman/fluorescence stimulator for cure monitoring are embraced within the scope of this invention. For example, numerical values and recitations of particular substances are illustrative rather than limiting. The laser can be replaced by a wavelength narrowed light emitting diode. Therefore, the present invention should be construed as limited only by the appended claims.

We claim:

1. A laser curing apparatus for performing a curing process on a material with real-time monitoring and control of the curing process, the laser curing apparatus comprising:
   (a) a laser element for emitting a laser beam at a wavelength selected to cure the material and to excite Raman/fluorescence emission from said material; and
   (b) an optical spectrometer element for receiving the Raman/fluorescence emission to measure a spectrum of said Raman/fluorescence emission in real time and determine curing status information regarding the curing process from the measured Raman/fluorescence spectrum.

2. The laser curing apparatus of claim 1, wherein the optical spectrometer element determines the curing status information from a variation of intensity and wavelength position of its Raman emission spectrum during the curing process.

3. The laser curing apparatus of claim 1, wherein the laser element is a diode laser, a solid-state laser, a gas laser or a wavelength narrowed light emitting diode.

4. The laser curing apparatus of claim 1, wherein the laser element produces light in the UV/VIS wavelength range for photochemical curing.

5. The laser curing apparatus of claim 1, wherein the laser element produces light in the NIR/IR wavelength range for thermal curing.

6. The laser curing apparatus of claim 1, wherein the laser element operates in CW mode.

7. The laser curing apparatus of claim 1, wherein the laser element operates in pulsed mode.

8. The laser curing apparatus of claim 1, wherein the optical spectrometer element comprises wavelength selective components and photo detectors or photo detector arrays, and wherein said wavelength selective components comprise gratings, interferometers, or tunable filters.

9. The laser curing apparatus of claim 1, wherein the optical spectrometer element comprises a plurality of wavelength-fixed filters and photo detectors.

10. The laser curing apparatus of claim 1, further comprising an output for outputting the curing status of the material obtained by the optical spectrometer element to an operator.

11. The laser curing apparatus of claim 1, further comprising a secondary optical system for controlling properties of the laser beam.

12. The laser curing apparatus of claim 11, further comprising a feedback control system that utilizes the curing status information of the material obtained by the optical spectrometer element to control the secondary optical system and the properties of the laser element in order to improve the curing process.

13. The laser curing apparatus of claim 12, wherein the feedback control system automatically turns off the laser element when the spectrometer element indicates that the curing process is finished.

14. A laser curing method for performing a curing process on a material with real-time monitoring and control of the curing process, the laser curing method comprising:
   (a) causing a laser beam to be incident on the material, the laser beam having a wavelength selected to cure the material and to excite Raman/fluorescence emission from said material;
   (b) measuring a spectrum of said Raman/fluorescence emission in real time;
   (c) determining curing status information regarding the curing process from the measured Raman/fluorescence spectrum; and
   (d) controlling properties of the laser beam according to said curing status information.

15. The laser curing method of claim 14, wherein step (c) comprises determining the curing status information from a variation of intensity and wavelength position of the Raman emission spectrum during the curing process.

16. The laser curing method of claim 14, wherein step (a) comprises generating the laser beam by use of a diode laser, a solid-state laser, a gas laser or a wavelength narrowed light emitting diode.

17. The laser curing method of claim 14, wherein the laser beam is in the UV/VIS wavelength range for photochemical curing.

18. The laser curing method of claim 14, wherein the laser beam is in the NIR/IR wavelength range for thermal curing.

19. The laser curing method of claim 14, wherein the laser beam is emitted in CW mode.

20. The laser curing method of claim 14, wherein the laser beam is emitted in pulsed mode.

21. The laser curing method of claim 14, wherein step (b) is performed with wavelength selective components and photo detectors or photo detector arrays, and wherein said wavelength selective components comprise gratings, interferometers, or tunable filters.

22. The laser curing method of claim 14, wherein step (b) is performed with a plurality of wavelength-fixed filters and photo detectors.

23. The laser curing method of claim 14, wherein step (d) is performed by a secondary optical system.

24. The laser curing method of claim 14, wherein step (d) further comprises automatically turning off the laser beam when the measured Raman/fluorescence spectrum indicates that the curing process is finished.

25. A curing apparatus for performing a curing process on a material with real-time monitoring and control of the curing process, the curing apparatus comprising:
- (a) a light emitting element for emitting a light beam at a wavelength selected to cure the material and to excite Raman/fluorescence emission from said material; and
- (b) an optical spectrometer element for receiving the Raman/fluorescence emission to measure a spectrum of said Raman/fluorescence emission in real time and determine curing status information regarding the curing process from the measured Raman/fluorescence spectrum.

26. A curing method for performing a curing process on a material with real-time monitoring and control of the curing process, the curing method comprising:

- (a) causing a light beam to be incident on the material, the light beam having a wavelength selected to cure the material and to excite Raman/fluorescence emission from said material;
- (b) measuring a spectrum of said Raman/fluorescence emission in real time;
- (c) determining curing status information regarding the curing process from the measured Raman/fluorescence; and
- (d) controlling properties of the laser beam according to said curing status information.

* * * * *